United States Patent [19]

Harding

[11] Patent Number: 4,689,935

[45] Date of Patent: * Sep. 1, 1987

[54] ANTISEPTIC GLOVE

[76] Inventor: Audrey E. Harding, 1087 Cork Dr., Bethel Park, Pa. 15102

[*] Notice: The portion of the term of this patent subsequent to Nov. 1, 1993 has been disclaimed.

[21] Appl. No.: 118,775

[22] Filed: Feb. 25, 1987

[51] Int. Cl.4 ............................................. B65D 81/22
[52] U.S. Cl. ..................................... 53/431; 206/210; 206/438
[58] Field of Search ............... 206/63.2 R, 63.3, 47 R, 206/7 F, 46 AP, 278, 299, 438–441, 205, 210; 53/431; 422/28

[56] References Cited

U.S. PATENT DOCUMENTS

| | | | |
|---|---|---|---|
| 2,491,015 | 12/1949 | Poole | 422/28 |
| 2,782,912 | 2/1957 | Humphrey | 206/47 R |
| 3,295,675 | 1/1967 | Burns et al. | 206/63.2 R |
| 3,315,802 | 4/1967 | Lonholdt et al. | 206/63.2 R |
| 3,326,450 | 6/1967 | Langdon | 206/63.2 R |
| 3,399,955 | 9/1968 | Zimmerman | 422/28 |
| 3,409,010 | 11/1968 | Kron | 206/278 |
| 3,409,121 | 11/1968 | Taterka | 206/299 |
| 3,608,566 | 9/1971 | Storandt | 206/63.5 |
| 3,720,037 | 3/1973 | Jones | 53/431 |

Primary Examiner—Stephen Marcus
Assistant Examiner—Jimmy G. Foster
Attorney, Agent, or Firm—Buell, Ziesenheim, Beck & Alstadt

[57] ABSTRACT

A method and apparatus for providing antiseptically sterile hands for use in hospitals where germ transfer from one patient to another is to be avoided, this being accomplished by encapsulating an antiseptically presoaked glove and later removing the encapsulating material to provide the user with premoistened gloves to perform body massage and operating room functions free of fear that there may be germ transfer to a patient under care.

2 Claims, 8 Drawing Figures

ANTISEPTIC GLOVE

This invention relates to a presoaked antiseptic glove. More specifically, this invention relates to both a method and apparatus for providing antiseptically sterile hands by the utilization of an antiseptically presoaked glove. These gloves are to be used in hospitals or any place where there is a fear of germ transfer from one patient or party to another patient or party. This is accomplished by encapsulating an antiseptically presoaked glove and later removing the encapsulating material to provide the user with premoistened gloves to perform body massages and operating room functions free of fear that there may be germ transfer to a patient or party under care.

In hospitals the country over, back massage is an everyday occurrence. Usually one nurse or nurse's aide will have many patients to care for in this manner. Theoretically after each back rub the nurse or nurse's aide is supposed to wash her hands, but with the shortage of nurses this procedure is circumvented by merely going from patient to patient with the common risk of spreading such germs as staph infection amongst the other patients. In addition, the operating room of the hospital must be germ-free and once a doctor has washed up he may not touch anything until he has his sterilized rubber operating gloves put on.

Both of these areas are greatly helped by the invention to be described hereinafter.

It is therefore an object of this invention to provide a sterile condition of the hands without regard to whether the hands are sterile before use of gloves that are antiseptic by their very nature.

The preferred embodiment of this invention is basically covered by the following method which is providing a sterilized glove in which the following steps are involved. Immersing a saturable glove in a solution having antiseptic qualities, then removing the saturable glove from the solution. This step is followed by draining the glove of excess solution. The next step involves the insertion of the glove between two layers of material having leakproof qualities, then sealing peripheral portions of the material to totally encapsulate the saturated glove.

The next step involves the shearing of the material that encapsulates the glove to expose for use by the wearer of the glove. The wearer of the glove is then provided with a hygenic glove which will not allow contamination of the wearer's hands or the transfer of germs from one patient or party to another.

Other objects and advantages of the invention will become apparent from the ensuing description of illustrative embodiments thereof, in the course of which reference is had to the accompanying drawings in which.

Figure 1:
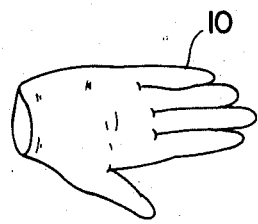
FIG. 1 illustrates a typical glove used in this invention.
Figure 1A:
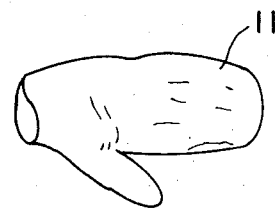
FIG. 1a illustrates a mitten that may be employed in this invention.
Figure 2:
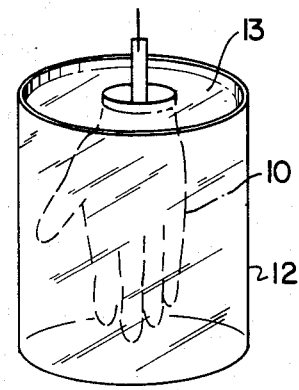
FIG. 2 shows a glove submerged in an antiseptic solution.
Figure 3:
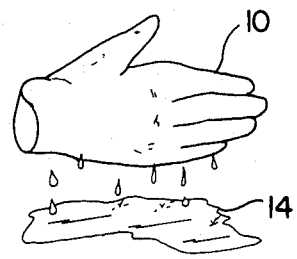
FIG. 3 shows a glove removed from said solution being drained of excess solution.
Figure 6:
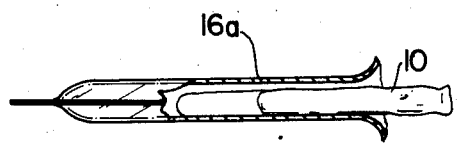
FIG. 6 shows the glove or mitten being removed for use.
Figure 5:
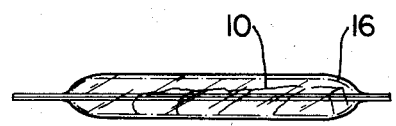
FIG. 5 shows the glove or mitten totally encapsulated.
Figure 4:
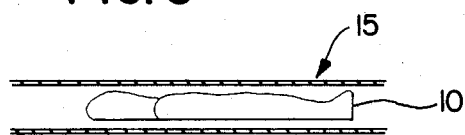
FIG. 4 shows two pieces of material and a glove which are to be encapsulated.
Figure 6A:
FIG. 6a shows a doctor or intern using the glove to protect his hands from contamination.

FIG. 1, as noted earlier in the specification, is directed to a glove. This glove, designated by the reference numeral 10, is a typical glove that would be worn by a doctor or a nurses's aide, or a nurse in fact. FIG. 1a shows a mitten configuration of the glove-type structure which is also included within the purview of this invention. FIG. 2 shows the step of placing in the antiseptic solution 13 a glove 10, the solution being contained in a container 12. FIG. 3 illustrates the removal of the glove 10 from the solution 13 and also depicts drainage of excess moisture or the antiseptic solution from the glove 10, as can be seen by the reference numeral 14. Once a glove has been drained of the excess solution it is now ready for encapsulation, as shown in FIG. 4. FIG. 4 shows two sheets of material that are impervious to moisture as designated by the reference numeral 15. The glove, of course, is designated by the reference numeral 10. When the outer peripheral portions of the impervious material are secured, either by a mechanical interlocking of the materials or an adhesive, we find ourselves with that which is depicted in FIG. 5. In FIG. 5, we see the glove 10 in dotted outline totally sealed from the outside environment and this is designated as finished product 16. In the event of the use of this invention, the glove 10 and impervious material 16a would be removed, as shown in FIG. 6, by shearing the outer peripheral portion of the glove holder. FIG. 6a shows a doctor, or a medical technician, utilizing the gloves that were encapsulated, as shown in FIG. 5. This encapsulation provides the doctor, or as it may be, the nurse, with a sterile glove which in turn can be utilized in the operating room prior to the operation that is to be performed, or in a more common area where a nurse is involved in the conventional back rubbing activity which takes place on numerous occasions during the day in a hospital. The wearing of the glove, or the mitten as it may be, is a highly significant advantage in view of the fact that the nurse of the doctor need not wash up between working with patients having various diseases or illnesses. There need only be a removal of the glove and a reopening of the second package, which has encapsulated therein, the glove itself. This is the important aspect of this invention, namely, that the glove itself has an antiseptic quality and it may be impregnated or saturated by alcohol or, more conventionally, in a body massage lotion which is antiseptic in itself.

It will therefore be seen that the invention described herein is an advantageous way of securing germicidal-free use of the hands by either a nurse or doctor. It should be noted that severe burn patients as well as abdominal surgery patients will also be protected.

It will also be apparent that other modifications and changes can be made to the presently described invention and therefore it is understood that all changes, equivalents, and modifications falling within the spirit and scope of the present invention are herein meant to be included in the appended claims.

Having thus described my invention, what I claim is:

1. A method for providing sterilized protective gloves including the following steps,
    (a) immersing a saturable glove capable of fully enclosing a wearer's hand and adapted to cover separately each of a wearer's fingers and thumb in a solution having antiseptic qualities to saturate the said glove with said solution,
(b) removing said saturable glove from said solution,
(c) draining said glove of excess solution to provide a glove saturated with said antiseptic solution,
(d) inserting said saturated glove between two layers of material having leakproof qualities,
(e) sealing peripheral portions of said material to totally encapsulate said saturated antiseptic glove,
(f) shearing said peripheral portions of said material that encapsulates said glove to expose for use by the wearer of the glove, said glove being saturated when removed and worn thereby providing the wearer with a hygenic glove saturated with said antiseptic solution which fully encloses the hand and separately covers each of a wearer's fingers and thumb and which will not allow contamination of said wearer's hands during the performance of routine operations.

2. The method of claim 1 wherein said glove is a mitten.

* * * * *

UNITED STATES PATENT AND TRADEMARK OFFICE
CERTIFICATE OF CORRECTION

PATENT NO. : 4,689,935

DATED : September 1, 1987

INVENTOR(S) : Audrey E. Harding

It is certified that error appears in the above-identified patent and that said Letters Patent is hereby corrected as shown below:

Title page:

In [22] change "1987" to --1971--.

In column 2, line 42, change the second occurance of "of" to --or--.

Signed and Sealed this

Twenty-ninth Day of December, 1987

Attest:

DONALD J. QUIGG

Attesting Officer

Commissioner of Patents and Trademarks